(12) United States Patent
Li

(10) Patent No.: US 9,216,341 B2
(45) Date of Patent: Dec. 22, 2015

(54) REAL-TIME SWIMMING MONITOR

(76) Inventor: Xipu Li, San Jose, CA (US)

( * ) Notice: Subject to any disclaimer, the term of this patent is extended or adjusted under 35 U.S.C. 154(b) by 393 days.

(21) Appl. No.: 12/484,226

(22) Filed: Jun. 14, 2009

(65) Prior Publication Data

US 2010/0030482 A1    Feb. 4, 2010

Related U.S. Application Data

(60) Provisional application No. 61/137,841, filed on Aug. 4, 2008.

(51) Int. Cl.
| | | |
|---|---|---|
| *G06F 19/00* | (2011.01) | |
| *G01C 21/00* | (2006.01) | |
| *A63B 69/12* | (2006.01) | |
| *A61B 5/11* | (2006.01) | |
| *G06K 9/00* | (2006.01) | |
| *G07C 1/22* | (2006.01) | |
| *A63B 33/00* | (2006.01) | |
| *A63B 71/06* | (2006.01) | |
| *A61B 5/00* | (2006.01) | |

(52) U.S. Cl.
CPC ............ *A63B 69/12* (2013.01); *A61B 5/1112* (2013.01); *A61B 5/1118* (2013.01); *A61B 5/1123* (2013.01); *G06K 9/00342* (2013.01); *G07C 1/22* (2013.01); *A61B 5/6803* (2013.01); *A61B 5/6823* (2013.01); *A61B 2503/10* (2013.01); *A61B 2505/09* (2013.01); *A61B 2562/0219* (2013.01); *A63B 33/002* (2013.01); *A63B 2071/063* (2013.01); *A63B 2071/0661* (2013.01); *A63B 2208/03* (2013.01); *A63B 2220/16* (2013.01); *A63B 2220/17* (2013.01); *A63B 2220/40* (2013.01); *A63B 2220/836* (2013.01)

(58) Field of Classification Search
CPC ............................ G06F 19/18; G06K 9/00342
USPC ............ 377/24.2; 702/19, 56, 139, 150, 160, 702/142, 155, 178, 213
See application file for complete search history.

(56) References Cited

U.S. PATENT DOCUMENTS

| | | | |
|---|---|---|---|
| 5,136,621 A * | 8/1992 | Mitchell et al. | ............... 377/24.2 |
| 5,258,785 A | 11/1993 | Dawkins | |
| 5,391,080 A * | 2/1995 | Bernacki et al. | ............... 434/254 |

(Continued)

FOREIGN PATENT DOCUMENTS

WO    WO 2008032315 A1 *   3/2008

OTHER PUBLICATIONS

James Dieble, "Representing Attitude: Euler Angles, Unit Quaternions, and Rotation Vectors", Oct. 20, 2006, Stanford University, pp. 1-35.*

(Continued)

*Primary Examiner* — Patrick Assouad
*Assistant Examiner* — Haidong Zhang
(74) *Attorney, Agent, or Firm* — HM Law Group LLP; Vani Moodley, Esq.

(57) ABSTRACT

A wearable device for monitoring and providing real-time feedback about a swimmer's body motion and performance, in particular, body orientation and forward speed, is provided. The device comprises a three-axis accelerometer, optionally a three-axis gyroscope, a memory, and a microcontroller configured to process the sensor input, calculate a swimmer's performance and provide feedback to the swimmer through an output. The output can be an earpiece or a swimming goggle with a digital display.

21 Claims, 19 Drawing Sheets

(56) References Cited

U.S. PATENT DOCUMENTS

| | | | |
|---|---|---|---|
| 5,402,188 A | | 3/1995 | Wayne |
| 5,585,871 A | | 12/1996 | Linden |
| 5,685,722 A | * | 11/1997 | Taba .......................... 434/254 |
| 5,921,890 A | | 7/1999 | Miley |
| 6,033,228 A | | 3/2000 | Ladin |
| 7,072,789 B2 | * | 7/2006 | Vock et al. .................. 702/141 |
| 2003/0189484 A1 | * | 10/2003 | Rust et al. ................ 340/323 R |
| 2005/0186542 A1 | | 8/2005 | Roncalez |
| 2006/0038718 A1 | * | 2/2006 | Arakane et al. .......... 342/357.11 |
| 2007/0006472 A1 | * | 1/2007 | Bauch .......................... 33/355 R |
| 2007/0013512 A1 | * | 1/2007 | Burneske et al. ........ 340/539.13 |
| 2007/0032951 A1 | * | 2/2007 | Tanenhaus et al. ........... 701/220 |
| 2007/0060452 A1 | * | 3/2007 | Chang ............................ 482/55 |
| 2008/0018532 A1 | * | 1/2008 | Mackintosh et al. .... 342/357.12 |

OTHER PUBLICATIONS

James R. Wertz, Spacecraft Attitude Determination and Control, p. 414, 1978, Kluwer Academic Publishers, Dordrecht, The Netherlands.

Arthur Gelb, Applied Optimal Estimation, pp. 107-111, 1974, The MIT Press, Cambridge, Massachusetts.

Sabra Chartrand, Patents; Inventors Create a High-Technology Swim Goggle, a Floating Word Game and a Better Sand Castle, The New York Times, Apr. 20, 1998, The New York Times Company, New York, New York.

* cited by examiner

REAL-TIME SWIMMING MONITOR

CROSS-REFERENCE TO RELATED APPLICATIONS

This Application claims the benefit of PPA Ser. No. 61/137,841, filed Aug. 4, 2008 by the present inventor.

FEDERALLY SPONSORED RESEARCH

Not Applicable

SEQUENCE LISTING OR PROGRAM

Not Applicable

FIELD OF THE INVENTION

The present invention relates to a method and system for monitoring a swimmer's performance and providing real-time feedback, particularly to a method and system for real-time measurement of a swimmer's body orientation and speed.

BACKGROUND OF THE INVENTION

In today's high tech era, it is becoming more and more common for recreational as well as competitive athletes to resort to technology for improving their performances. Swimming, in particular, is a sport where technique is intricate and strongly correlated to performance level. As many swimming experts have pointed out, a swimmer's body orientation and coordination is the most important factor in achieving optimal performance. Without a streamlined body formation, the forces exerted by a swimmer's strokes and kicks do not efficiently translate to speed, and may even hinder the swimmer's performance. Currently, swimmers rely heavily on observations from a coach or video footage to identify flaws in and possible improvements to their technique. However, such methods necessarily occur in a non real-time fashion, and thus prevent the swimmer from instantaneously and clearly recognizing body motion that contributes to enhanced performance. Real-time feedback is particularly important in swimming because many aspects of the sport are opposite to human intuition; a swimmer's "feel" about his performance is usually inaccurate. For example, a swimmer may put in extra effort during a particular lap but end up with an unexpected slower split time due to poor technique. Conversely, it is also common for a swimmer to unexpectedly achieve a better split time during a relaxed set. It would therefore be advantageous to have systems and methods that provide technique and performance feedback to swimmers in real-time. Such systems and methods would allow a swimmer to adjust his technique in the middle of a set in response to such feedback, and observe the performance consequences. Swimmers may use these systems and methods during training to identify techniques that most effectively translate to improved performance.

SUMMARY OF THE INVENTION

The present invention provides simple, practical, and accurate means for monitoring a swimmer's performance and providing real-time feedback. In particular, in one embodiment, the invention discloses a wearable monitoring system that provides real-time monitoring of a swimmer's body orientation, speed, and other performance information so that the swimmer can instantly correlate his body motion with performance and constantly adjust his technique and effort level to meet training goals.

The disclosed system comprises an electronic device and an output unit. The electronic device may be a device encased in a waterproof case and worn by a swimmer at the small of the back, on the abdomen, or on the back of the head. The output unit may be an earpiece or a pair of swimming goggles with an integrated digital display. The electronic device may communicate with the output unit through a wire or wireless communication technology.

The electronic device primarily comprises a 3-axis accelerometer, a microcontroller and a memory unit. The accelerometer provides measurements of the acceleration produced by the swimmer's strokes and the gravitational force. The microcontroller is configured with embedded programs to receive accelerometer measurements and calculate the swimmer's body orientation and forward speed.

Optionally, a 3-axis gyroscope may be included in the electronic device to improve a swimmer's body orientation calculation using body angular rate provided by the gyroscope. The rotational rate measurements from the gyroscope combined with the measurements made from the accelerometer provide a six degree-of-freedom description of the swimmer's body motion, which is a comprehensive description of the swimmer's body motion. The six degree-of-freedom body motion kinematics equations can then be solved to obtain accurate body orientation and forward speed.

The body orientation and speed calculations can be further improved by including one or more position sensors. These sensors are used to compensate for drift errors introduced by integrating acceleration or body rate due to the accelerometer/gyroscope output noises. The Kalman Filter algorithm may be employed to process the position sensor data and provide an optimal compensation. For pool swimming, the position sensor may be a photoelectric sensor detecting pool markings such as black lane markings commonly found on swimming pool floors. For open water swimming, where the drift error can be more significant, a GPS receiver may be used as the position sensor.

The memory unit in the electronic device can be a flash memory or a memory circuitry internal to the microcontroller. The memory unit is used for storing performance data that can be displayed after a workout or downloaded to a personal computer for further analysis.

The data output for real-time feedback to a swimmer, via an earpiece or a swimming goggle with a digital display, may be speed, body rotation angles, swimming time, split time, lap counts, and stroke counts, among other things.

DETAILED DESCRIPTION OF THE INVENTION

Figure 1:
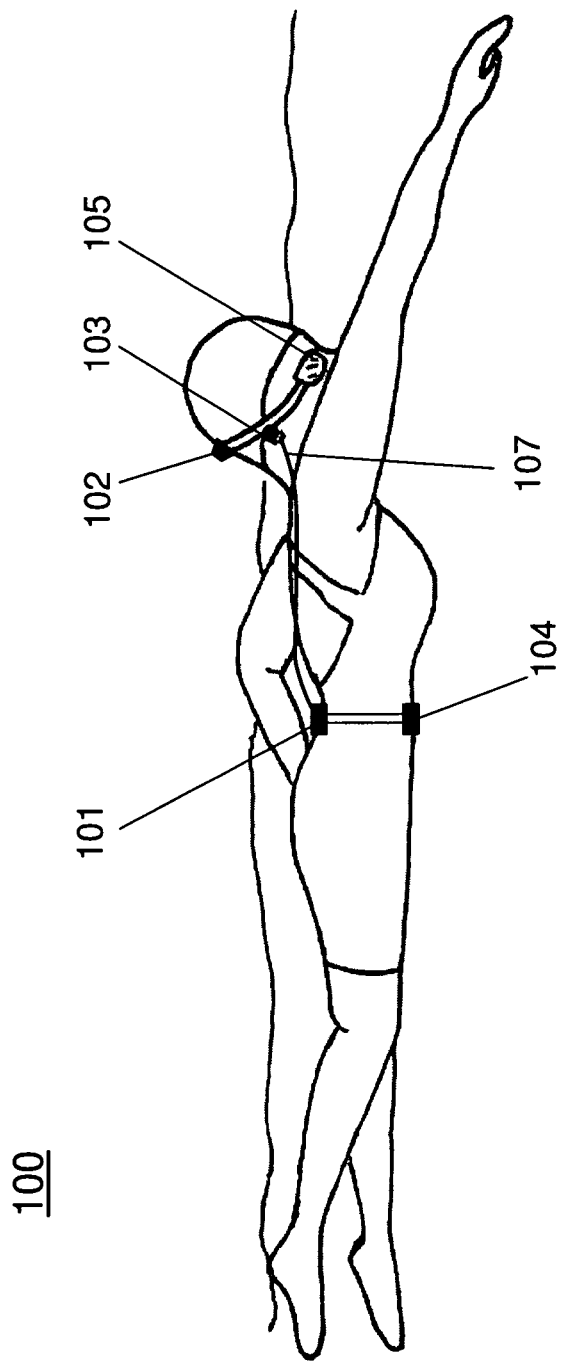
FIG. 1 shows a perspective view of one embodiment of the invention, comprising an electronic device and an output unit.

The present invention provides a wearable data acquisition and processing system configured to measure a swimmer's body motion and performance. As shown in FIG. 1, the disclosed system 100 comprises an electronic device with an output unit. The electronic device may be a device worn at the small of the back 101, on the abdomen 104, or on the back of the head 102. The output may be an earpiece 103 or a pair of swimming goggles with an integrated digital display 105. The system 100 is encased in a waterproof case. The electronic device (101, 102, or 104) provides real-time motion measurements and feedback of the swimmer's performance through the output unit (103, 105) to the swimmer. The electronic device (101, 102, or 104) may communicate with the output unit (103, 105) through a wire (107) or wireless communication technology.

Figure 2A:
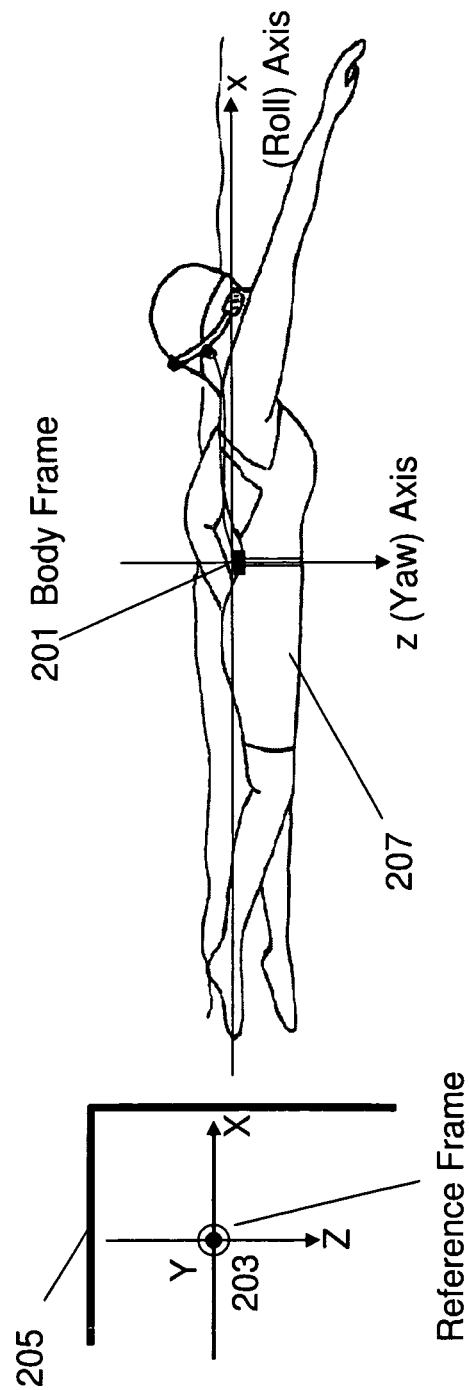
FIGS. 2A and 2B show the definitions of a swimmer's body orientation with respect to a reference coordinate system.
Figure 2B:
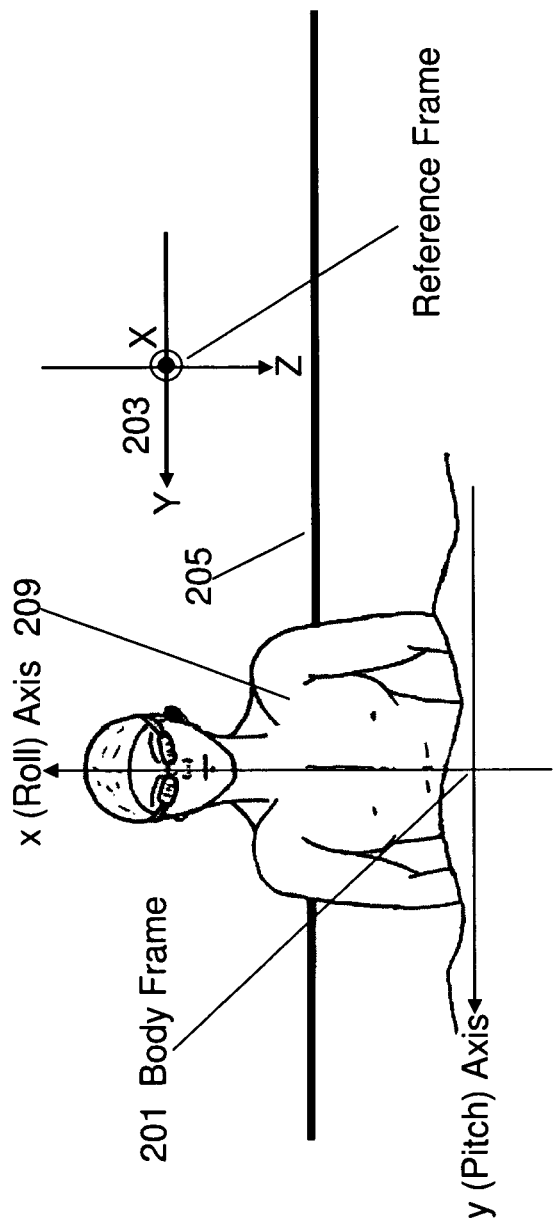

A swimmer's motion includes a swimmer's forward speed and body orientation with respect to the swimmer's surroundings. FIGS. 2A and 2B provide an exemplary description of a swimmer's body orientation in terms of two coordinate systems: a body frame x-y-z 201 and a reference frame X-Y-Z 203. The body frame 201 is fixed to the body of a swimmer (207 or 209): x-axis, designated as roll axis, is parallel to the swimmer's longitudinal axis; y-axis, designated as pitch axis, is parallel to the swimmer's lateral axis (from left to right); and z-axis, designated as yaw axis, is orthogonal to both x and y axes, running from the swimmer's back to the front. The electronic device would be conveniently worn on the swimmer's body such that the 3 axes of the accelerometer are essentially aligned with the body frame x-y-z. The reference frame 203 is fixed to the swimming pool structure 205. The reference frame 203 can also be fixed with respect to other landmarks, such as buoys, the shoreline, or other landmarks for open water swimmers. In FIG. 2A, the body frame 201 for swimmer 207 is aligned with the reference frame 203. In contrast, the body frame 201 for swimmer 209 in FIG. 2B is not aligned with the reference frame 203, since he is in a standing (vertical) orientation. Note that a convenient definition of the reference frame 203 is such that the Z axis is parallel to the direction of gravity.

Figure 3A:
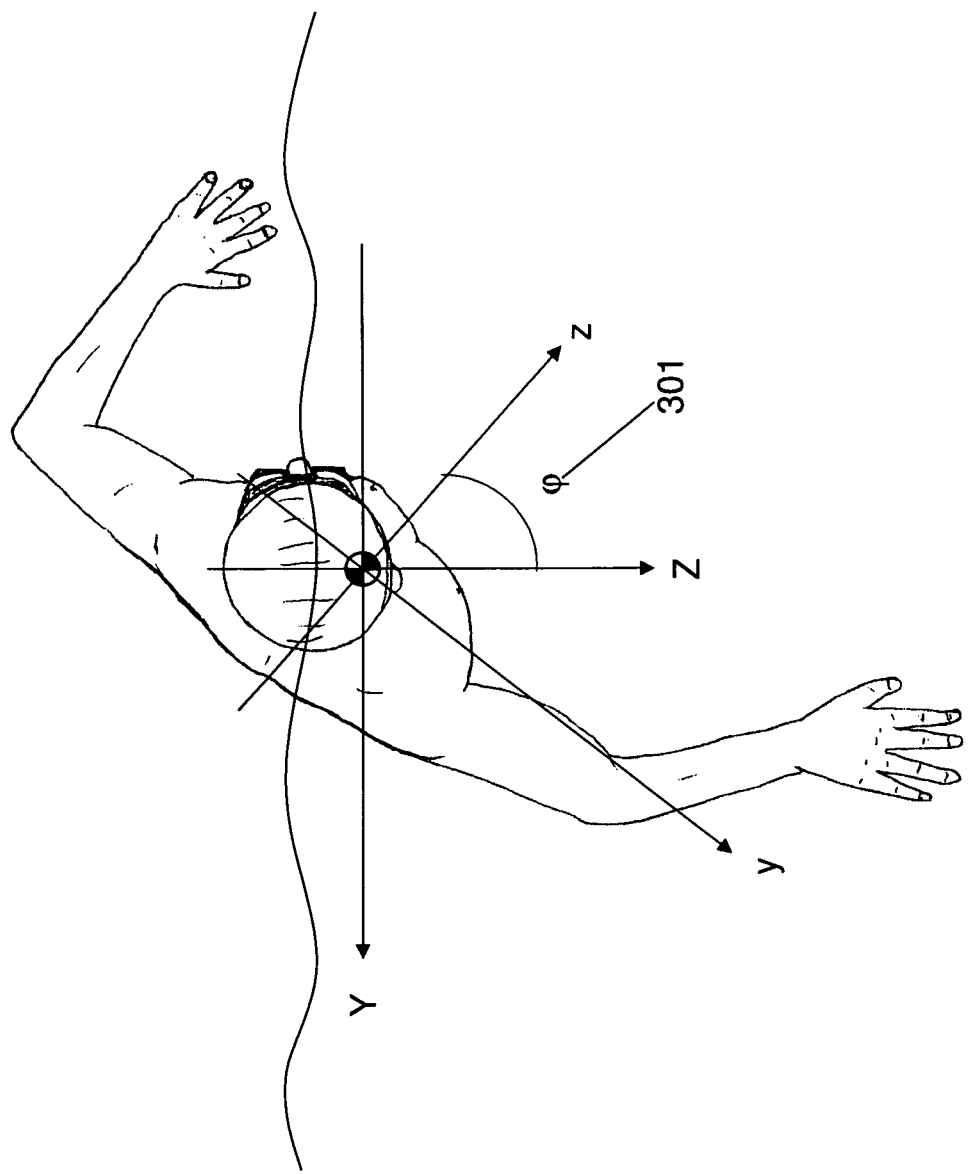
FIGS. 3A, 3B, and 3C show a swimmer's body orientation in terms of Euler angles.
Figure 3B:
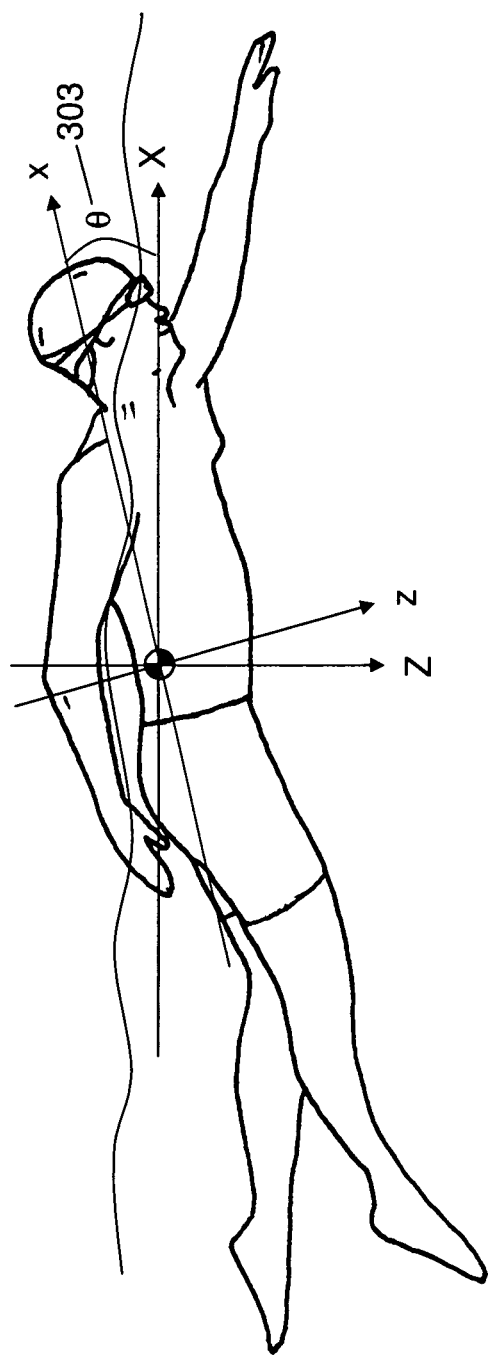
Figure 3C:
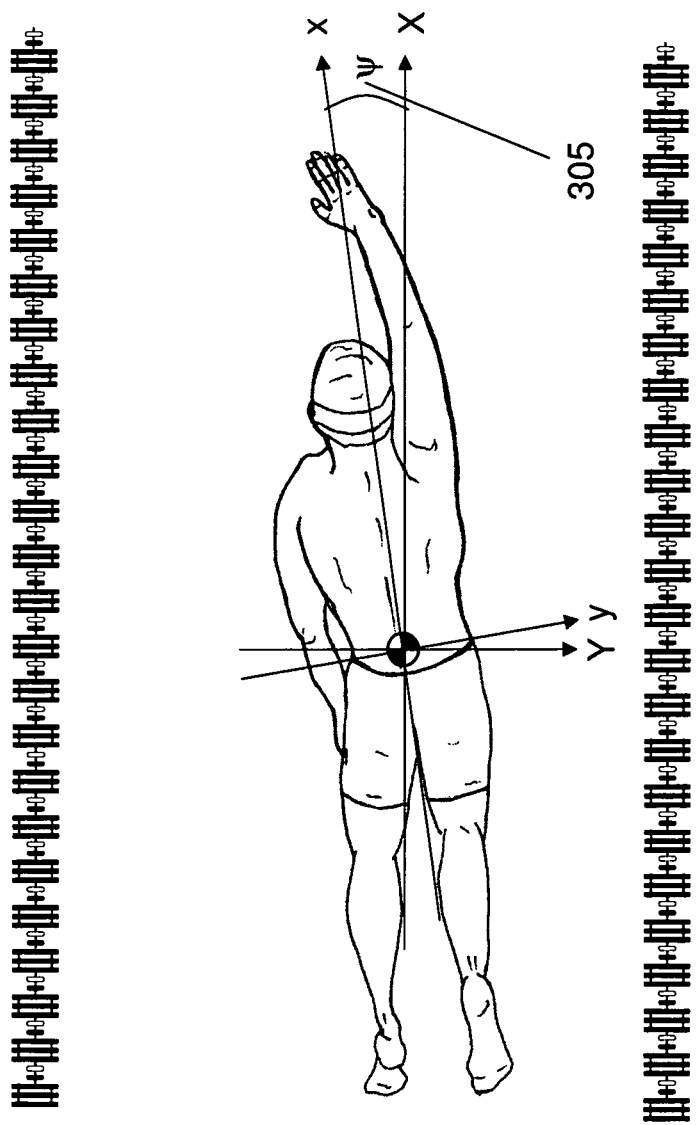

With the above definitions of the coordinate systems, a swimmer's body orientation may be described quantitatively by the angular deviation of the body frame 201 from the reference frame 203 in terms of Euler angles, namely, roll, pitch, and yaw angles. The Euler angles $\phi$ (roll) 301, $\theta$ (pitch) 303, and $\psi$ (yaw) 305 are described in FIGS. 3A, 3B, and 3C, respectively. It is well-known that a freestyle swimmer should maintain large roll angles 301 (hip rotations) and small pitch 303 and yaw 305 angles for optimal performance. Roughly speaking, a large roll angle 301 increases the effectiveness of the strokes, whereas small pitch 303 and yaw 305 angles keep the swimmer's body in streamline. As described in the following paragraphs, the disclosed system measures these angles and the swimmer's speed in forward direction (X-axis), and provides the swimmer feedback about his body form in real-time.

Figure 4:
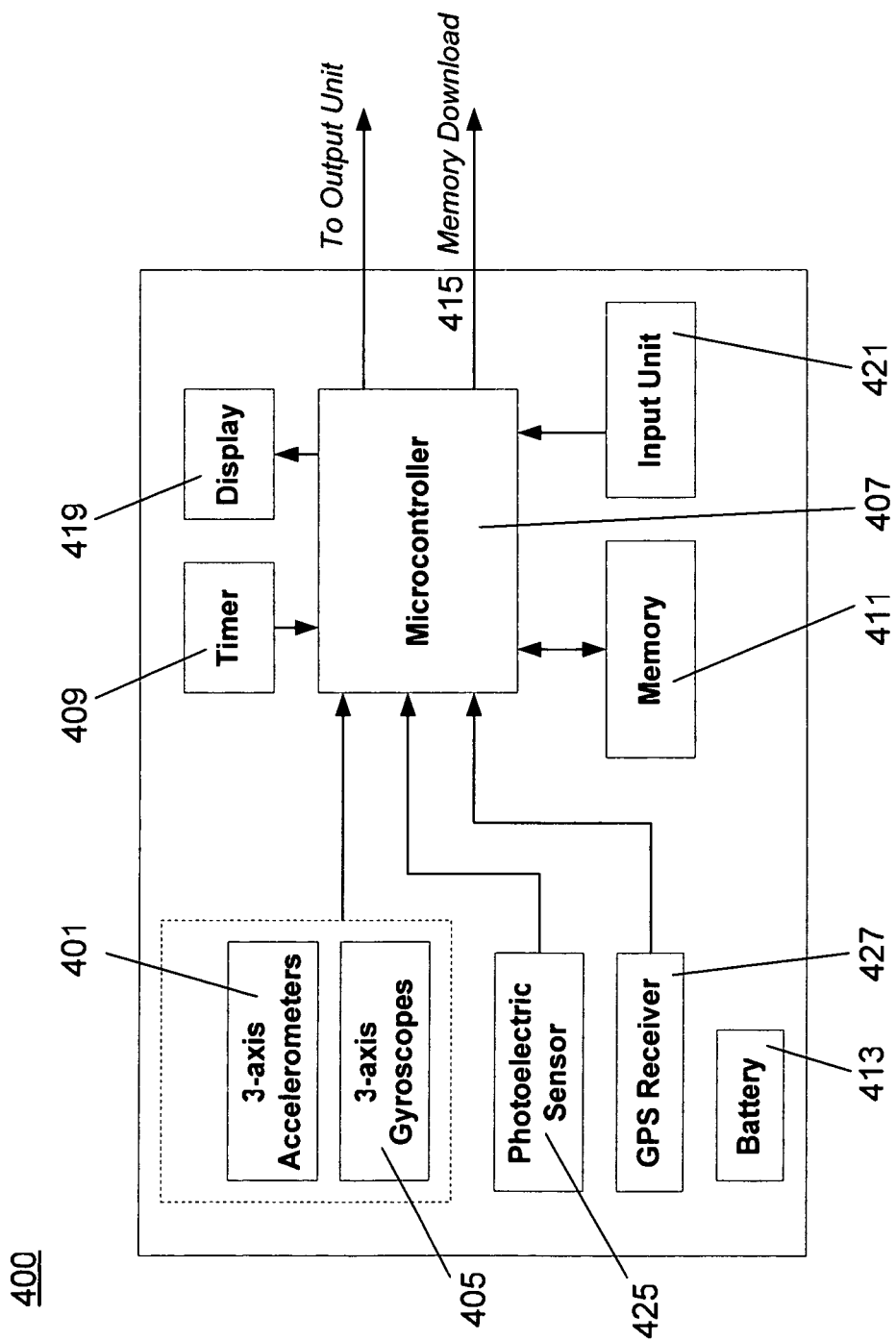
FIG. 4 is a block diagram of one implementation of the electronic device of FIG. 1.

With reference now to FIG. 4, there is shown an exemplary electronic device 400 that can be used to implement electronic device (101, 102, 104) of FIG. 1. Device 400 may comprise a 3-axis accelerometer unit 401, a microcontroller unit 407, a memory unit 411, a battery unit 413, and a timer 409 for the device. The accelerometer 401 provides measurements of the acceleration produced by the swimmer's strokes and the gravitational force. The accelerometer 401 may be conveniently worn on the swimmer such that its three axes are each parallel to the x, y, and z axes of body frame 201 defined in FIG. 2, respectively.

The microcontroller 407 is configured with embedded computer programs to periodically receive, at a selected sampling rate, measurements made by accelerometer 401. The microcontroller 407 uses the received measurements to calculate in real-time the swimmer's instant body orientation by determining the amplitude of the gravitational component along each axis of the accelerometer 401. In other words, the microcontroller 407 determines the angular differences in two dimensions between the reference frame 203 and the body frame 201 as defined in FIG. 2.

The microcontroller 407 also calculates the speed of the swimmer by integrating acceleration in the forward direction. The forward direction can be defined to be in the direction of the X-axis in reference frame 203 of FIG. 2. The forward speed may be calculated by mapping the accelerometer measurements, which are made with respect to body frame 201, to the reference frame 203, and integrating the component along the X-axis of reference frame 203. Thus, the orientation of body frame 201 with respect to reference frame 203 is necessary for the speed calculation. Note that since a three-axis accelerometer cannot provide complete rotational information, the swimmer's translational and rotational motion cannot be completely decoupled. This may lead to imperfect body orientation and speed calculations.

However, this shortfall can be overcome by also including in electronic device 400 a three-axis gyroscope 405. The output of gyroscope 405 is the rate of change of roll angle ($\phi$) 301, pitch angle ($\theta$) 303, and yaw angle ($\psi$) 305, as previously defined in FIG. 3. The rotational rate measurements provided by gyroscope 405 combined with the measurements made by accelerometer 401 provide a six degree-of-freedom description of the swimmer's body motion, which is a comprehensive description of the swimmer's body motion. The six degree-of-freedom body motion kinematics equations can then be solved to obtain accurate body orientation and the forward speed.

The body orientation and speed calculations can be further improved by including calibration means. In general, integration of sensor output can introduce drift error over time due to the accumulation of sensor noise and/or bias. Calibration can serve to compensate for the drift error. Accordingly, electronic device 400 may optionally include one or more photoelectric sensors 425 to provide swimmer position information that can be used to estimate and cancel the drift error. In one embodiment, photoelectric sensors 425 may be configured to detect markings in the swimmer's surroundings. These markings can be, for example, black lane markings commonly found on swimming pool floors and walls, or colored lane lines. These markings are particularly useful because they generally are located at standardized locations along competition-sized pools.

Another way to provide calibration means is to include a GPS receiver 427 in device 400 that can provide location measurements to microcontroller 407. GPS receiver 427 may be particularly useful for open water swimming, where accelerometer and/or gyroscope drifts can be more significant.

The calibration scheme employed by microcontroller 407 can be based on a Kalman Filter optimal estimation algorithm. A Kalman Filter algorithm optimally weighs the position measurements obtained from the calibration means, such as photoelectric sensors 425 or GPS receiver 427, to correct for drift errors in the speed and body orientation values computed by integration.

With continued reference to FIG. 4, device 400 may also include memory unit 411. Memory 411 can be a flash memory or a memory circuitry internal to microcontroller 407. Microcontroller 407 may periodically or continuously store sensor data and calculated information into the memory, thereby creating a history of the swimmer's body motion and performance. The length of time between consecutive storages (sampling rate) can be programmed into microcontroller 407 as a design parameter.

The body orientation calculations and the sensor measurements described above can be further processed to determine a swimmer's mode of activity. A swimmer's mode of activity can be, for example, diving into the pool, taking a stroke, gliding, doing a turn, pushing off a wall, standing vertically, and stopping at the end of a lap. In an exemplary embodiment, microcontroller 407 determines the swimmer's current mode of activity by looking at a combination of both the current sensor inputs and body orientation calculations and also the history data stored in memory 411, as described in the previous paragraph. Specifically, microcontroller 407 may look at the swimmer's mode of activity at the last time step to determine the mode of activity at the current time step.

Referring back to FIG. 4, device 400 may also include a timer unit 409. Timer 409 can be internal or external to microcontroller 407. In some embodiments, timer 409 can be driven by a crystal oscillator. Timer 409 can include a master timer that is incremented by microcontroller 407. Device 400 may use the master timer for synchronization of internal activities; however, the master timer value can also be outputted to the user. In addition to a master timer, Timer 409 can also include one or more split timers. The split timer can be used by the swimmer to record split times of each lap. Advantageously, the split timer can be automatically reset based on changes in the swimmer's mode of activity. Specifically, microcontroller 407 may reset the split timer each time the mode of activity is "pushing off the wall", as described above. The split timer values can also be stored periodically in memory 411.

In addition to automatically resetting the split timer, the mode of activity information can also be used to automatically record the swimmer's stroke count per lap or total stroke count. The microcontroller 407 may determine the stroke count by tracking the number of times the swimmer's mode of activity is "taking a stroke" between consecutive split timer resets or as a running total. The stroke count can also be periodically stored in memory 411.

When the swimmer's mode of activity is gliding or stroking, microcontroller 407 may use the calculated body orientation to determine the amplitude of the swimmer's hip rotation (along the roll axis 301, FIG. 3, for example). The microcontroller 407 may be programmed with a predetermined range of acceptable hip rotation amplitude values, preferably determined by a swimming expert. When the swimmer's hip rotation falls outside of the acceptable range, microcontroller 407 may output a warning to the swimmer informing him of the deviation from good swimming form.

Figure 5:
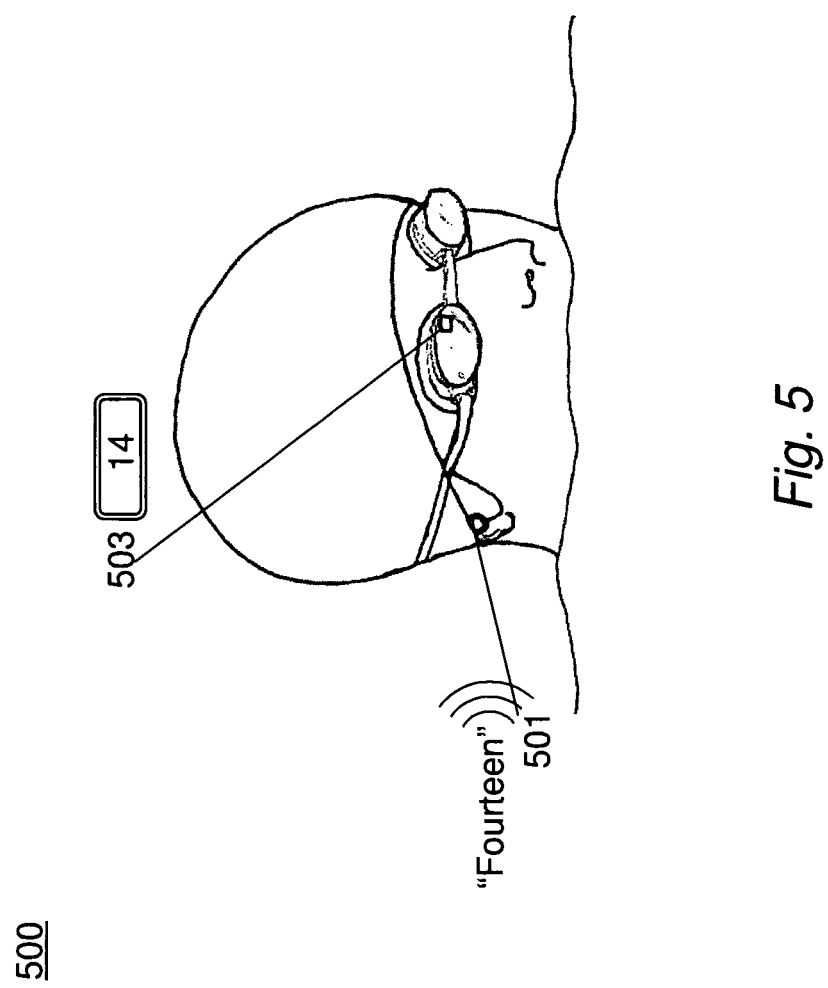
FIG. 5 shows a perspective view of an exemplary output unit of FIG. 1.

Referring now to FIG. 5, there are shown two exemplary output devices that can be used to implement output device 103 and 105 in FIG. 1. Exemplary output device 501 is an earpiece that the swimmer can wear while swimming. Output device 501 may be connected to device 400 via a wire or wireless technology. Output device 501 may provide the swimmer with feedback about his performance. This may include hip rotation warnings, as described above, instantaneous speed, and the master timer or split timer values, for example. Alternatively, the same performance feedback can also be provided visually to the swimmer via output device 503, which is a display mounted onto a goggle. In this manner, the swimmer's performance is provided to the swimmer in real-time while he is swimming.

In addition to the information provided to the swimmer in real-time, device 400 of FIG. 4 can also provide a summary of the workout to the swimmer in response to a request by the swimmer. The workout summery may include, for example, the average stroke court per lap, average split time, average speed, and the total workout time and distance. The workout summary may be provided through output devices 501 or 503, or another type of output device such as a wristwatch or a display integrated into device 400.

Referring back to FIG. 4, device 400 may optionally include an input unit 421. Input unit 421 can be used by the swimmer to provide device 400 with additional information. Such additional information may include, for example, the type of stroke the swimmer is planning on swimming, whether he is in a pool or in open water, and what kind of feedback the swimmer desires to receive through the output device 501 or 503. Such additional information may be used in the calculation of body orientation and speed. Input unit 421 may include push buttons that may be used to navigate a control menu that is provided to the swimmer via a display 419. Display 419 may be a display integrated into device 400, or may be the same display as in output device 503. The control menu may also be an audio control menu that may be navigated using input 421 via output 501.

In addition to providing real-time feedback and workout summaries through the various output devices, the sensor raw data and calculated performance data stored in memory 411 may also be downloaded to a personal computer for further analysis through communication interface 415. Interface 415 may be, for example, a USB port. The downloaded raw data and processed data (e.g., the time histories of body orientation and speed) may be used to reconstruct the swimmer's performance and detailed body motions for ex post analysis, perhaps by a coach or swimming expert.

Figure 6:
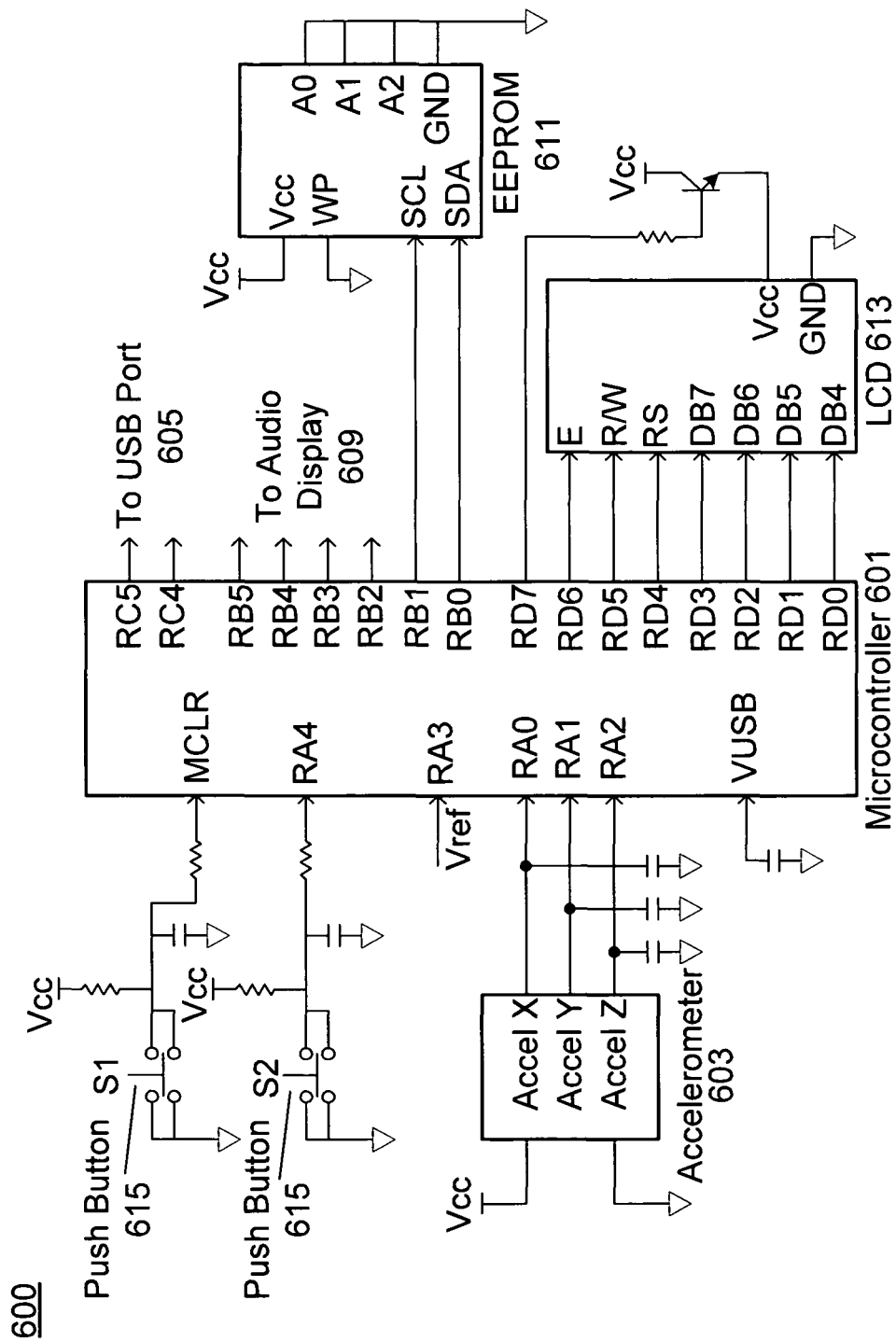
FIG. 6 is a schematic drawing of one embodiment of the electronic device of FIG. 4.

Now with reference to FIG. 6, there is shown schematic diagram of one implementation 600 of device 400. Implementation 600 uses microcontroller 601, which can be, for example, PIC18F4550 from Microchip Technology and accelerometer 603 ADXL 330 from Analog Devices. The memory unit 611 can be a non-volatile Electrically Erasable Programmable Read-Only Memory (EEPROM) integrated circuit chip.

Figure 7:
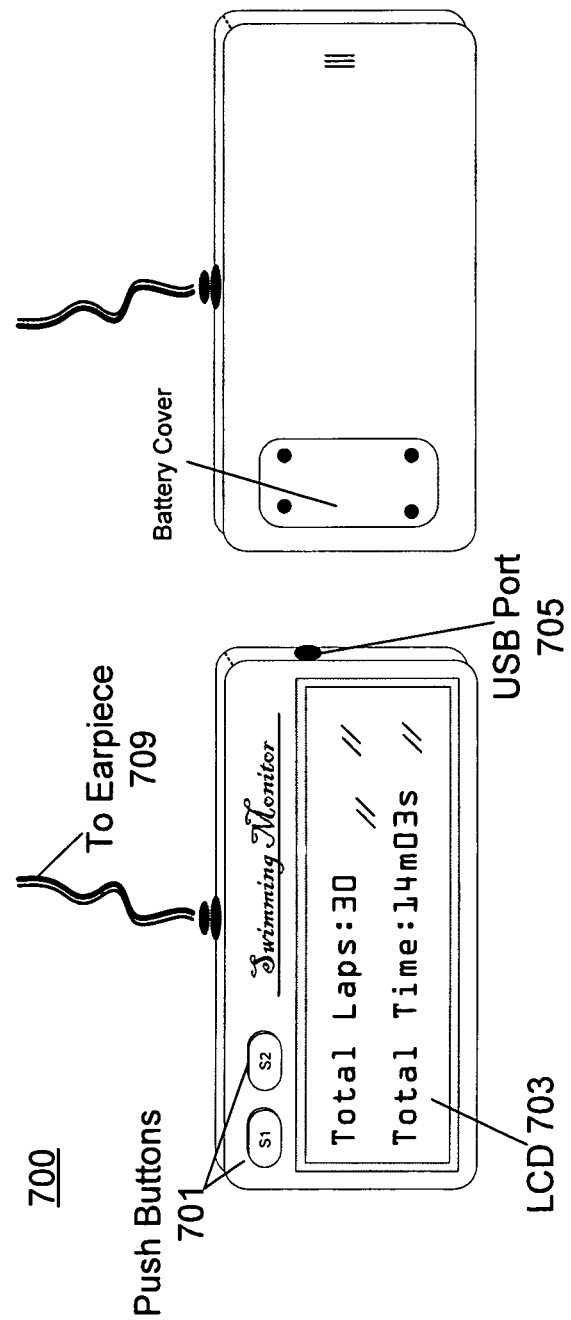
FIG. 7 shows a perspective view of one possible exterior appearance of the electronic device of FIG. 1.

FIG. 7 shows the exterior appearance of one embodiment of the invention. The electronic device is encased in a waterproof case that is wearable on a swimmer's body near his center of gravity (CG) such as the small of the back or abdomen, or on the back of the head. The device is worn by a swimmer such that the x-y-z axes of the accelerometer are parallel to the body x-y-z axes (FIG. 2). That is, the x-axis of the accelerometer is along the swimmer's longitudinal axis (body x-axis) and z-axis of the accelerometer is aligned with the gravity direction when the swimmer is floating horizontally. The device 700 connects to the output unit 501 or 503 (FIG. 5) by wire 709. A wireless technology can alternatively be used. A prospective user may use push buttons 701 and a liquid crystal display 703 to turn on/off the device and navigate the operation menu. Instead of display 703, the menu can also be provided audibly through earpiece 501, for example. The USB port 705 may be used to download the stored data to a personal computer for further analysis.

Figure 8A:
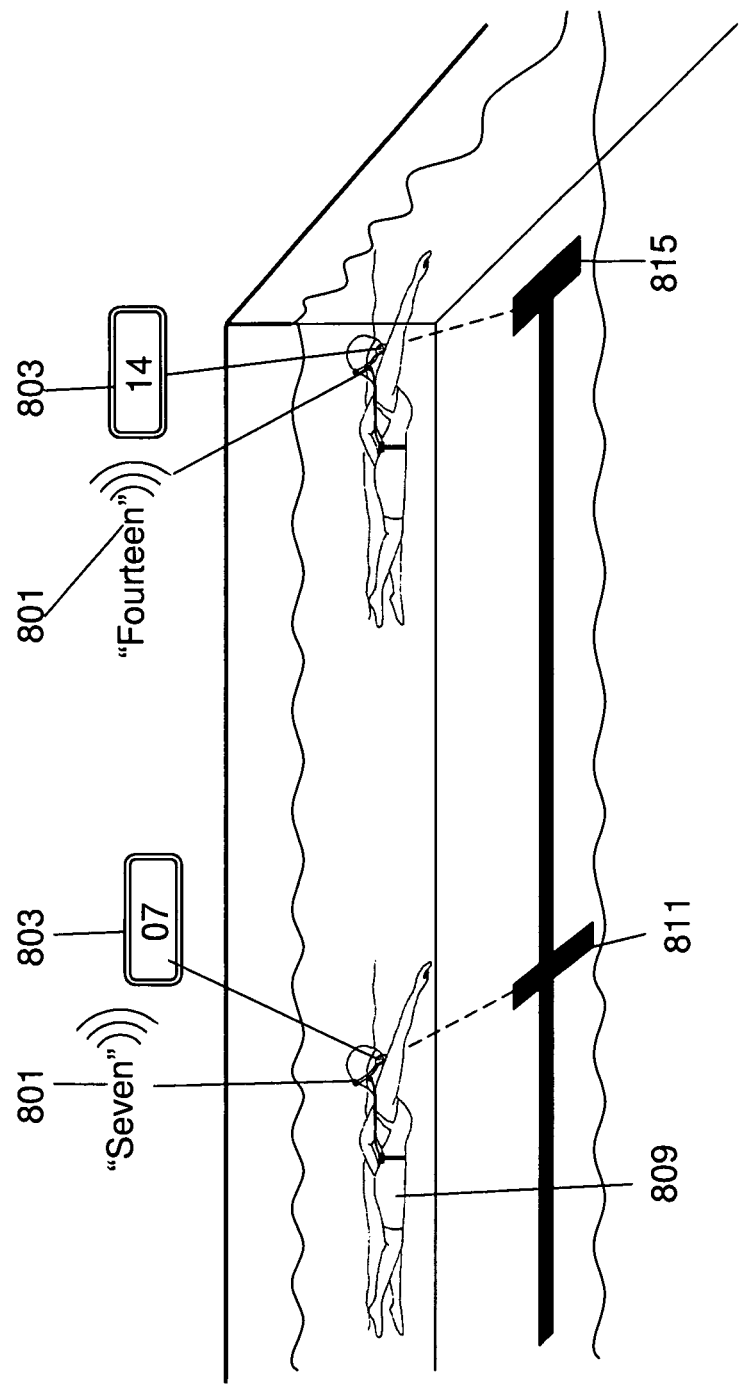
FIGS. 8A and 8B show a perspective view of how one embodiment of the present invention may be used by a swimmer in a swimming pool.
Figure 8B:
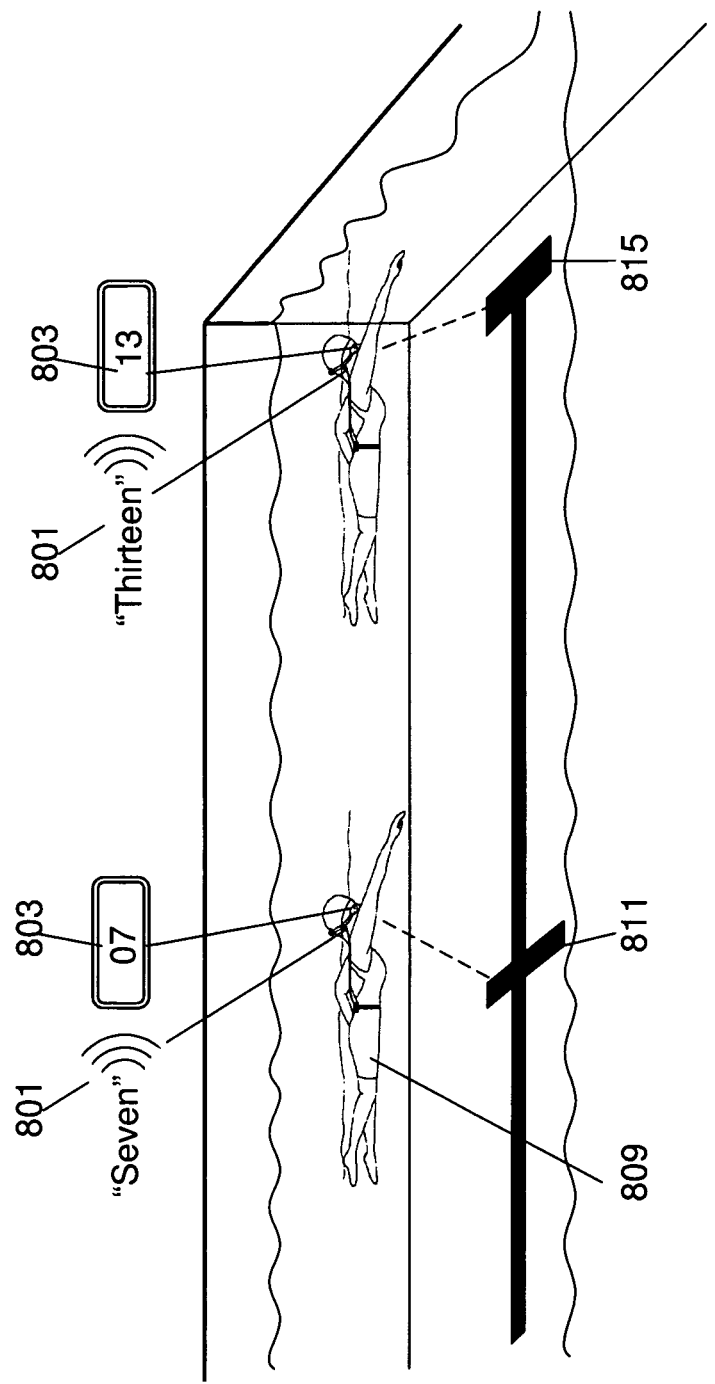

FIGS. 8A and 8B demonstrate one particularly simple but still advantageous use of the present invention for providing a swimmer with real-time performance feedback. As previously described, device 400 of FIG. 4 can periodically provide swimmer 809 with the value of the timer 409. The value of the timer can be the total elapsed time from the start of the workout or the elapsed time from the beginning of a lap, as maintained by the split timer. The value of the timer may be the actual time value in minutes or seconds, or it may be a "count" value that is proportional to the actual elapsed time. The value of the timer can be provided to swimmer 809 audibly via earpiece 801 or visually via display 803. In FIG. 8A, swimmer 809 is shown to receive a count value of "seven" when she is at one location in the pool; the count has incremented to "fourteen" by the time she reaches the end of the pool. By periodically receiving the elapsed time value, the swimmer can monitor the timing of the passages of certain landmarks in the swimming pool (e.g., markers 811 and 815) during the course of swimming. The swimmer may use this information to compare with her previous performance (e.g., an earlier lap in the same set), and adjust her technique and effort level accordingly. The advantage of using the timer function to evaluate the speed, instead of directly using the calculated speed, is its simplicity and accuracy in operation, requiring less concentration on the fluctuating instant speed. Swimmers have their own benchmark performance to compare with in a relative manner, which does not need an accurate absolute speed at all times.

In the exemplary scenario shown in FIG. 8A, the timer starts when swimmer 809 initiates a new lap. The signal sent to the earpiece is the elapsed time counts. It may be announced in English, or another selected language, or certain audio tunes. For example, the elapsed time count 801 is announced as "one, two, three, . . . " in every 2 seconds. As illustrated, the earpiece says "seven" when swimmer 809 passes the middle line mark 811. That is, it takes swimmer 809 fourteen seconds to reach the middle line mark 811. When the swimmer reaches the end line 815, the earpiece 805 announces "fourteen." With an adjustment of her technique, the swimmer 809 in FIG. 8B realizes that this adjustment is effective when she passes the middle line mark 811 before "seven" is announced in the earpiece 801. As the result, the swimmer reaches the end line 815 when "thirteen" is announced.

Figure 9:
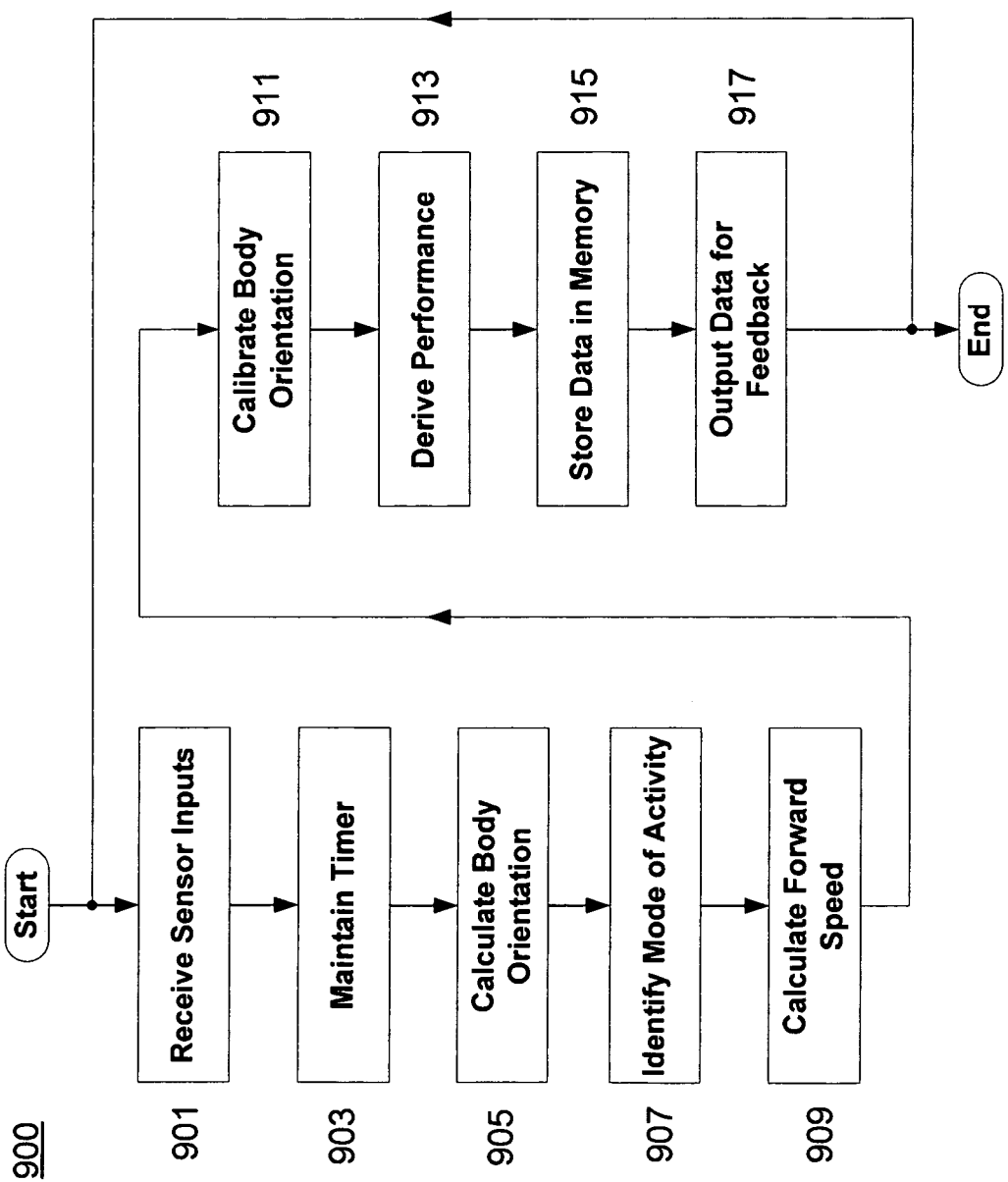
FIG. 9 shows a flowchart generally describing a method of measuring and providing feedback about a swimmer's body motion and performance.

In FIG. 9, there is shown a flowchart generally describing a method of measuring and providing feedback about a swimmer's body motion and performance. At step 901, measurements are received from a sensor worn by the swimmer. The sensor may be an accelerometer or a gyroscope or both. The sensor data may be processed by a microcontroller with embedded programs. At step 903, a timer value is maintained. At step 905, a swimmer's body orientation is calculated. At step 907, based on the body orientation and acceleration, a swimmer's mode of activity is identified. At step 909, a swimmer's forward swimming speed is calculated. At step 911, additional position sensor data may optionally used to calibrate the calculated body orientation and forward speed. The position sensor may be a photoelectric sensor or a GPS receiver. At step 913, a swimmer's performance data is extracted from the body motion information and formatted for storage and output. At step 915, a swimmer's body motion and performance data is stored in a memory. At step 917, a swimmer's performance is outputted to the swimmer for real time feedback. In the following paragraphs, more detailed disclosures are given for each of these steps.

Figure 10:
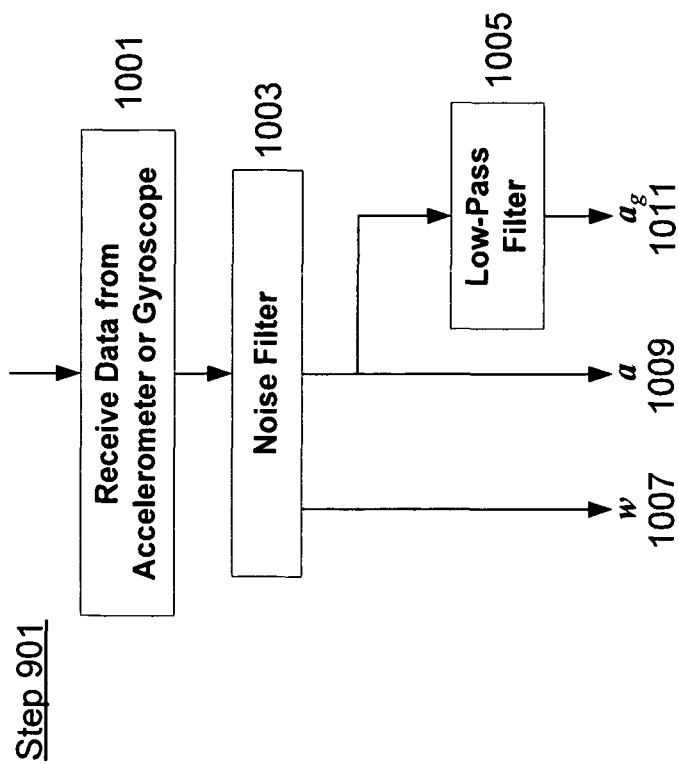
FIGS. 10-14 further describe the details of each step in FIG. 9.

With reference to step 901 in FIG. 9, there is shown a flow chart FIG. 10 further describing the sensor data receiving and processing function. At step 1001, raw sensor data is received from an accelerometer or a gyroscope. At step 1003, a low-pass filter may be applied to the raw sensor data to eliminate high frequency sensor noises, where a (1009) and w (1007) are the filtered, three dimensional acceleration and angular rate vectors, respectively. At step 1005, another low-pass filter may be applied to acceleration a to extract gravity vector $a_g$ (1011) from a (1009). This method is effective because that the gravity is constant in amplitude and of low frequency in directional variation in swimmer's body frame compared to the acceleration from swimmer's strokes.

Figure 11:
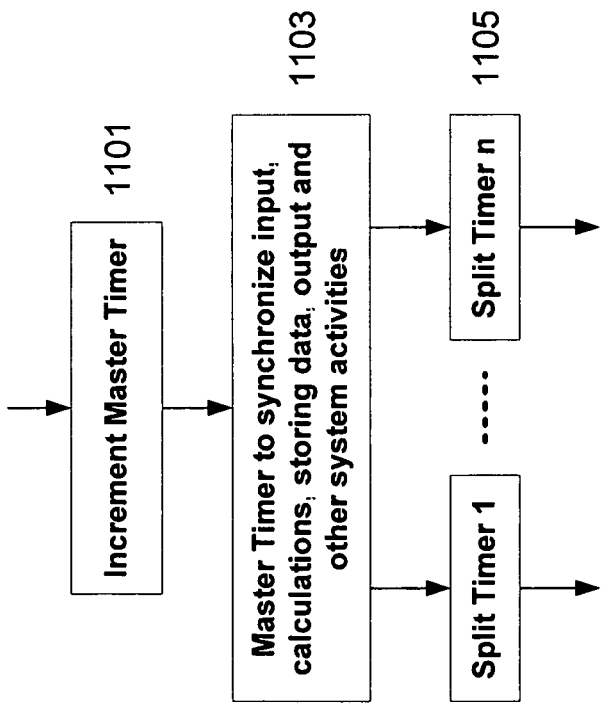

With reference to step 903 in FIG. 9, there is shown a flow chart FIG. 11 further describing the timer function. The timer can be a master timer that is continuously incremented as shown at step 1101. At step 1103, the master timer may serve as a timing reference for synchronization of system operations such as input/output, computations, storing data, and other activities. At step 1105, the master timer may also drive one or more split timers for various functions. A split timer may be synchronized with the local time and may be reset manually by a user or autonomously by the embedded program in the microcontroller when certain motion conditions are met.

Figure 12A:
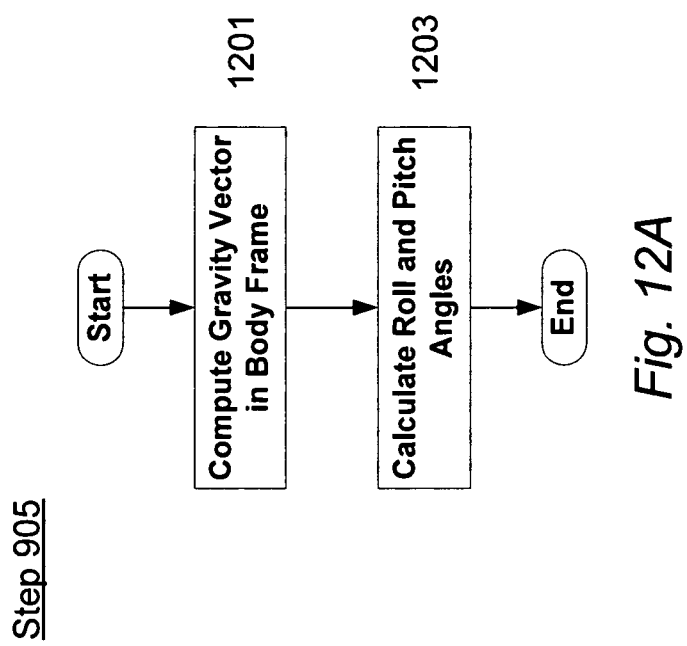

With continued reference to FIG. 9, at step 905, there is shown a flowchart in FIG. 12A further describing the method of calculating a swimmer's body orientation using the accelerometer input only. The body orientation calculation using both accelerometer and gyroscope data is described later in FIG. 12B. At step 1201, a three dimensional vector of gravity in the body frame 201 (FIG. 2) is calculated by Eq. 1.

$$a_g = \begin{bmatrix} Accel_x \\ Accel_y \\ Accel_z \end{bmatrix} \quad (1)$$

where $Accel_x$, $Accel_y$, and $Accel_z$ are input from the 3-axis accelerometer after passing low-pass filter 1005 (FIG. 10). Note that although most high-frequency acceleration components may have been filtered out by filter 1005, the body frame gravity vector $a_g$ (1011) may still include residual accelerations due to swimmer's strokes or other motions, therefore, the calculation of the gravity in body frame may not be very accurate. Essentially, this is an estimation method that may result in imperfect body orientation calculations. This shortfall, however, can be overcome by using a gyroscope; the method of which will be disclosed next. At step 1203, the body roll angle φ (301) and pitch angle θ (303), which are defined in FIG. 3, are calculated by Eqs. 2 and 3 with respect to the reference frame that is defined in FIG. 2

$$\varphi = \arctan \frac{Accel_y}{Accel_z} \quad (2)$$

$$\theta = \arctan \frac{-Accel_x}{Accel_z} \quad (3)$$

Figure 12B:
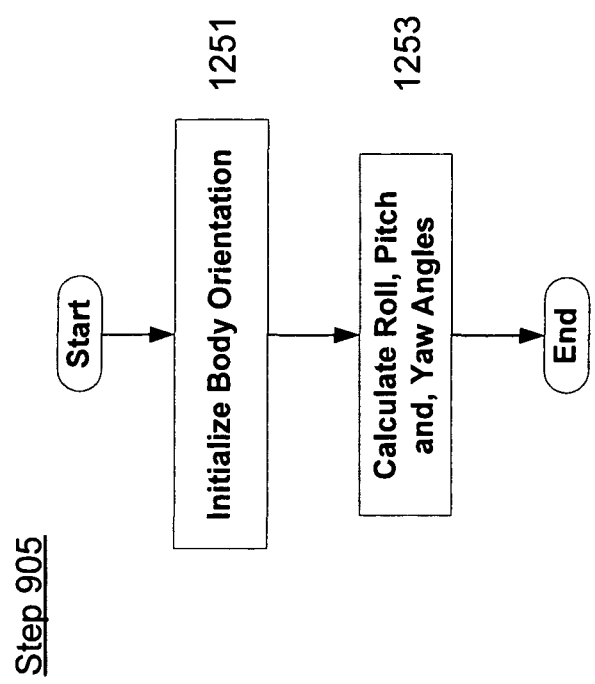

In FIG. 12B, there is shown a flowchart further describing the body orientation calculation using gyroscope data. With a 3-axis gyroscope, complete body rotational information of a swimmer can be obtained. The complete description of a body orientation with respect to a reference frame may be expressed by a quaternion. A quaternion is a 4-dimensional vector that is used to represent an arbitrary body orientation with respect to a reference frame. A quaternion q is defined by the following equation.

$$q = \begin{bmatrix} q_1 \\ q_2 \\ q_3 \\ q_4 \end{bmatrix} = \begin{bmatrix} e\sin(\frac{\alpha}{2}) \\ \cos(\frac{\alpha}{2}) \end{bmatrix} \qquad (4)$$

where $$e = \begin{bmatrix} e_1 \\ e_2 \\ e_3 \end{bmatrix}$$

is the unit rotation vector from the reference frame to the body frame and a is the rotation angle. For example, refer to FIG. 2B, the quaternion representing the body orientation of swimmer 209 is $$q = \begin{bmatrix} 0 \\ 0.707 \\ 0 \\ 0.707 \end{bmatrix} \qquad (5)$$

This is because that the swimmer's body orientation is obtained by rotating 90 degrees about y-axis from the swimmer's initial orientation that is aligned with the reference frame like swimmer 207 in FIG. 2A. Therefore, $$e = y\text{-axis} = \begin{bmatrix} 0 \\ 1 \\ 0 \end{bmatrix} \qquad (6)$$

and $$\alpha = 90 \text{ degrees} \qquad (7)$$

A unit quaternion is $$q = \begin{bmatrix} 0 \\ 0 \\ 0 \\ 1 \end{bmatrix} \qquad (8)$$

which represents a body frame that is aligned with the reference frame (a=0).

At step 1251, a swimmer's body orientation (quaternion) may be initialized to Eq. 5, if a swimmer is in standing position facing the far end of the pool like swimmer 209 in FIG. 2B. The initialization may be achieved by pushing a button on the device. This initialization may be performed once at the beginning of a swimming session or at any time when a swimmer is in the standing and the far-end-facing position. The quaternion may also be initialized autonomously, which may be triggered by the acceleration impulse from pushing off the wall to start a new lap. In this case, the initial value can be calculated using Eq. 4, based on the direction of gravity in the body frame. For example, if the accelerometer shows that the gravity is aligned with z-axis at the push-off, then the quaternion can be initialized to Eq. 8. One advantage of the autonomous initialization is that the gyroscope drift can be eliminated from regularly resetting the orientation to a known state.

With an initial value $q_0$, the swimmer's body quaternion can be propagated as a function of time t per step 1253 using the body angular rate sensed from the gyroscope.

$$q(t) = \exp\left(\frac{1}{2}\int_0^t \Omega(\tau)d\tau\right)q_0 \qquad (9)$$

where exp( ) is the matrix exponential function, $$\Omega = \begin{bmatrix} 0 & \omega_z & -\omega_y & \omega_x \\ -\omega_z & 0 & \omega_x & \omega_y \\ \omega_y & -\omega_x & 0 & \omega_z \\ -\omega_x & -\omega_y & -\omega_z & 0 \end{bmatrix} \qquad (10)$$

and $$w = \begin{bmatrix} \omega_x \\ \omega_y \\ \omega_z \end{bmatrix}$$

is body angular rate vector from the gyroscope. To convert the quaternion to Euler angles, the following equation may be used.

$$\begin{bmatrix} \varphi \\ \theta \\ \psi \end{bmatrix} = \begin{bmatrix} q_1 \\ q_2 \\ q_3 \end{bmatrix} \frac{360}{\pi} \qquad (11)$$

where $\phi$, $\theta$, and $\psi$ are roll, pitch and yaw angles in degrees, respectively.

Figure 13:
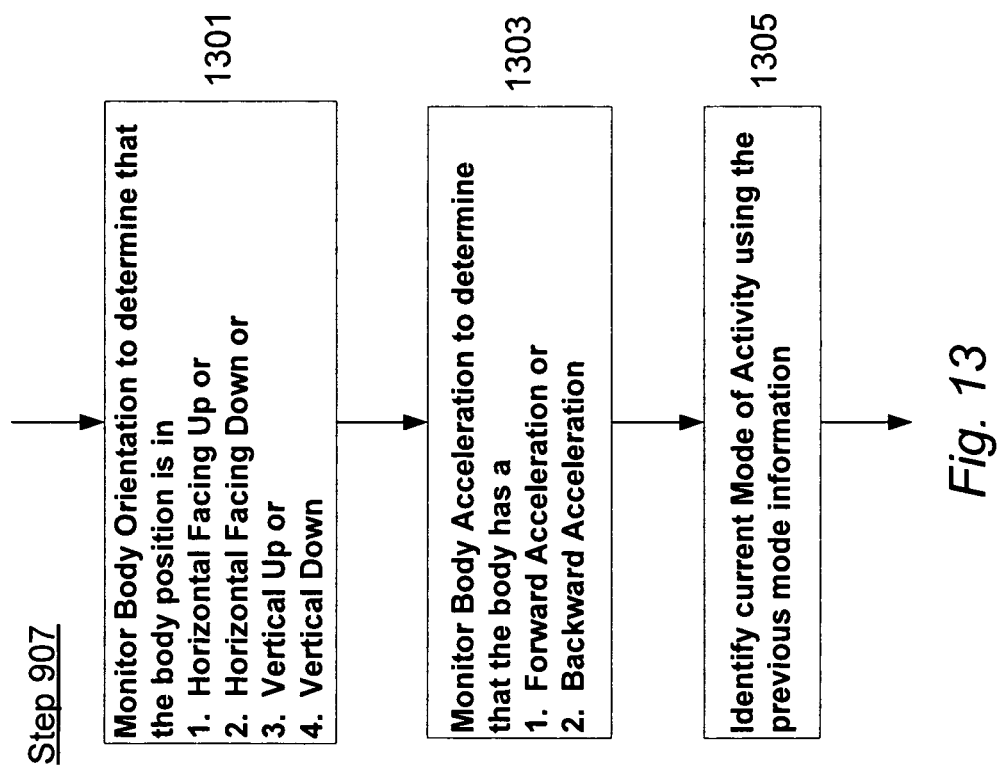

With continued reference to FIG. 9, at step 907, there is shown a flowchart in FIG. 13 further describing the identification of mode of activity. At step 1301, based on the previously calculated body orientation, a swimmer's body orientation is identified, for example, to be one of the four categories: horizontal facing up, horizontal facing down, vertical up and vertical down. When a swimmer is standing, he is in vertical up position. When a swimmer is making a flip turn, his position will be vertical down and then transitioned to horizontal up. When a swimmer is gliding or stroking in freestyle, his position is horizontal down. At step 1303, impulsive accelerations along the body x-axis is monitored to further distinguish a gliding mode from stroking mode and confirm a push-off start mode or a stop mode. Step 1305 further confirms the current mode of activity using the previous mode information. For example, a flip turn mode is likely to be transitioned to from a gliding mode.

With continued reference to FIG. 9, at step 909, the forward speed of a swimmer is calculated by integrating acceleration in the forward direction. Note that the body x-axis of a swimmer may not be perfectly aligned with the desired swimming direction (X-axis); therefore, the speed from integrating the x-axis acceleration may not be accurate. This scenario can be seen in FIG. 3C, where the side-way speed component would be undesirably included in the forward speed calculation. The reason for this error is that the yaw angle v is not observable to the accelerometer. However, this shortfall can be overcome by using the swimmer's body quaternion derived from a gyroscope (Eq. 9). When the quaternion is used, the forward speed can be obtained by integrating the acceleration along X-axis, instead of x-axis. This method consists of the following two steps.

$$\bar{a} = \begin{bmatrix} q_1^2 - q_2^2 - q_3^2 + q_4^2 & 2(q_1q_2 + q_3q_4) & 2(q_1q_3 - q_2q_4) \\ 2(q_1q_2 - q_3q_4) & -q_1^2 + q_2^2 - q_3^2 + q_4^2 & 2(q_2q_3 + q_1q_4) \\ 2(q_1q_3 + q_2q_4) & 2(q_2q_3 - q_1q_4) & -q_1^2 - q_2^2 + q_3^2 + q_4^2 \end{bmatrix} \times a \quad (12)$$

$$v_{cal} = \int_0^t [1 \ 0 \ 0] \times \bar{a} dt \quad (13)$$

where a (1009, FIG. 10) is a swimmer's acceleration in the body frame obtained from the accelerometer, $\bar{a}$ is the swimmer's acceleration in the reference frame and $v_{cal}$ is the swimmer's speed in the forward direction.

Figure 14:
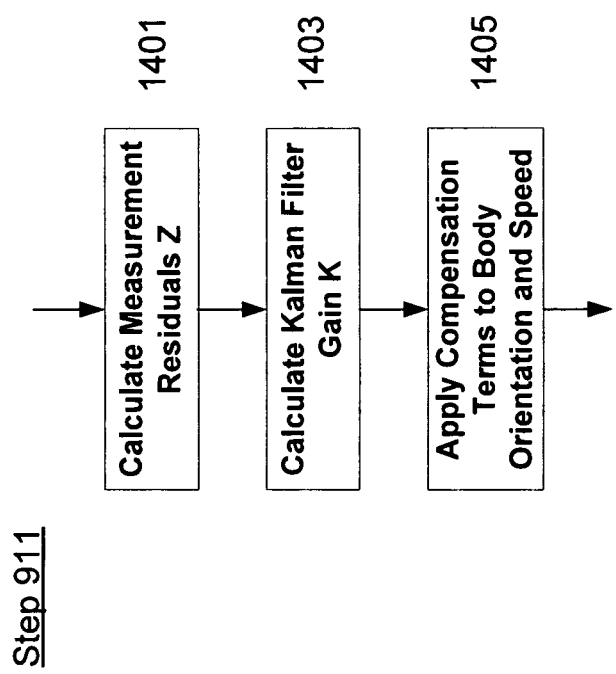

With continued reference to FIG. 9, at step 911, there is shown a flowchart in FIG. 14 further describing how the calculations of body orientation and forward speed can be further improved by including calibration means. In general, integration of sensor output can introduce drift error over time due to the accumulation of sensor noise and bias. Calibration can serve to compensate for the drift error using additional independent position data. The data may be produced by a photoelectric sensor or a GPS receiver mounted on a swimmer's body. For example, a photoelectric sensor, which detects certain pool markings such as black lane markings commonly found on swimming pool floors, can be used to calibrate the forward speed and accelerometer bias. The calibration method at step 911 comprises three major steps as shown in FIG. 14, which follows the optimal estimation theory, in particular, Kalman Filter algorithm. The following simple example is given so that the insight of the mathematics of Kalman Filter algorithm can be understood.

Referring back to FIG. 8A, if the location of the middle line mark 811 is known, then the expected mark passing time is $$t_{exp} = \frac{d_{mark}}{v_{cal}} \quad (14)$$

where $v_{cal}$ is the calculated forward speed and $d_{mark}$ is the distance of mark 811 from the pool's starting wall. Using the photoelectric sensor to take a snapshot at the split timer when the sensor detects its crossing mark 811, then the measured mark passing time $t_{mea}$ is obtained. At step 1401, the measurement residual is calculated by $$z = t_{mea} - t_{exp} \quad (15)$$

The residual z may be used to correct the calculated forward speed $v_{cal}$ and compensate for the accelerometer bias by the following equations.

$$v_{cal} = v_{cal} - K_v z \quad (16)$$

$$a = a - K_a z \quad (17)$$

where a (1009, FIG. 10) is a swimmer's acceleration in the body frame obtained from the accelerometer, $K_v$ and $K_a$ are "gains" for speed and acceleration compensations. The gains are used to weight how much compensation should be applied to the speed and acceleration using the residuals. Since noise also exists in photoelectric sensor output, it is not desirable to apply the compensation excessively. In fact, based on the sensor noise characteristics, optimal gains can be calculated using the Kalman Filter algorithm (step 1403). Once the Kalman Filter gains are calculated, at step 1405, the speed and acceleration are compensated by Eqs. 16 and 17, respectively.

Although the above discussion is about speed and accelerometer bias calibrations, the same logic applies to the body orientation and gyroscope bias calibrations.

With continued reference to FIG. 9, at step 913, a swimmer's performance can be extracted from his body motion data calculated above. The performance data, including a swimmer's instant speed, average speed, hip rotations, pitch and yaw angles, split time, stroke counts per lap, total laps, and other data, is formatted for storage at step 915 and output at step 917.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A wearable data acquisition and processing device configured to measure a swimmer's body motion and performance, the device comprising:
   a three-axis accelerometer;
   a three-axis gyroscope;
   a memory;
   an output device; and
   a microcontroller configured to:
      receive three-dimensional acceleration measurements from the accelerometer;
      receive three-dimensional angular velocity measurements from the gyroscope;
      calculate in real-time the swimmer's body orientation by calculating an angular deviation of a body frame (x,y,z) from a reference frame (X,Y,Z); wherein the body frame is fixed relative to the swimmer, and the reference frame is fixed relative to a swimming pool structure; said deviation being measured in terms of Euler angles;
      calculate in real-time the swimmer's speed in a forward direction by integrating acceleration in the forward direction using quaternion data for the swimmer obtained from the gyroscope and integrating acceleration along the X-axis of the reference frame;
      increment a timer;
      periodically store in the memory the three-dimensional acceleration measurements, the three-dimensional angular velocity measurements, the swimmer's speed in the forward direction, and the swimmer's body orientation; and periodically output to the output device the timer value, the swimmer's speed in the forward direction, and the swimmer's body orientation; and calibration means to compensate for drift errors in outputs from the accelerometer and the gyroscope;

wherein the device is configured to be initialized to a particular body orientation of the swimmer corresponding to when the swimmer is in a standing position facing a far end of the pool: wherein the calibration means comprises at least one photoelectric sensor configured to detect markings in the swimmer's surroundings, and wherein the microcontroller is further configured to use the detected markings information from the at least one photoelectric sensor to calibrate the swimmer's velocity in the forward direction, and the swimmer's body orientation.

2. The wearable device defined in claim 1, wherein the initialization is performed at the beginning of a swim session.

3. The wearable device defined in claim 1, wherein the initialization is performed autonomously.

4. The wearable device defined in claim 1, wherein the initialization is triggered by an acceleration impulse corresponding to when the swimmer pushes of a wall of the swimming pool to start each new lap.

5. The wearable device defined in claim 1, wherein the microcontroller is further configured to determine in real-time the swimmer's mode of activity, wherein the mode of activity is selected from a group comprising:
  diving;
  gliding;
  stroking;
  standing;
  turning;
  pushing off a wall; and
  stopping; and
  wherein the mode of activity is determined from at least one of the swimmer's body orientation and the three-dimensional acceleration.

6. The wearable device defined in claim 3, wherein the timer further comprises a split timer that resets when the swimmer's mode of activity is pushing off the wall or diving, and wherein the microcontroller is further configured to periodically store the split timer values into the memory.

7. The wearable device defined in claim 4, wherein the microcontroller is further configured to record in the memory the number of times the swimmer's mode of activity is stroking between a consecutive pair of split timer resets.

8. The wearable device defined in claim 1, wherein the microcontroller is further configured to output a warning signal to the output device when the swimmer's body orientation is outside a predetermined range of values.

9. The wearable device defined in claim 1, wherein content in the memory is downloadable to a personal computer for further analysis.

10. The wearable device defined in claim 1, further comprising a GPS receiver configured to provide location measurements to the microcontroller, and wherein the microcontroller is further configured to use the provided location measurements to calibrate the swimmer's speed in the forward direction.

11. The wearable device defined in claim 7, further comprising an input device that provides input to the microcontroller, and wherein the microcontroller is further configured to:

calculate a workout summary comprising at least one of an average swimmer's velocity in the forward direction, average stroke count between split timer resets, number of turns and final timer value; and output the workout summary to the output device based on the provided input.

12. The wearable device defined in claim 1, wherein the output device is an earpiece.

13. The wearable device defined in claim 1, wherein the output device is a display attached to a goggle.

14. A method of measuring and providing feedback about a swimmer's body motion and performance, the method is performed by a microcontroller, the method comprising:

receiving three-dimensional acceleration measurements from an accelerometer;

receiving three-dimensional angular velocity measurements from a gyroscope;

calculating in real-time the swimmer's body orientation by calculating an angular deviation of a body frame (x,y,z) from a reference frame (X,Y,Z); wherein the body frame is fixed relative to the swimmer, and the reference frame is fixed relative to a swimming pool structure; said deviation being measured in terms of Euler angle;

calculating in real-time the swimmer's speed in a forward direction by integrating acceleration in the forward direction using quaternion data for the swimmer obtained from the gyroscope and integrating acceleration along the X-axis of the reference frame;

incrementing a timer;

periodically store in a memory the three-dimensional acceleration measurements, the three-dimensional angular velocity measurements, the swimmer's speed in the forward direction, and the swimmer's body orientation;

periodically outputting to an output device the timer value, the swimmer's speed in the forward direction, and the swimmer's body orientation;

performing a calibration operation to compensate for drift errors in outputs from the accelerometer and the gyroscope;

performing an initialization operation to initialize to a particular body orientation of the swimmer corresponding to when the swimmer is a standing position facing a far end of the swimming pool structure;

outputting, to the output device, a warning signal when the swimmer's body orientation is outside a predetermined range of values;

receiving at least one user input;

calculating a workout summary comprising at least one of an average swimmer's velocity in the forward direction, average stroke count between split timer resets, number of turns and total workout duration; and outputting, to the output device, the workout summary based on the at least one user input.

15. The method defined in claim 14, wherein the initialization is performed at the beginning of a swim session.

16. The method defined in claim 14, wherein the initialization is performed autonomously.

17. The method defined in claim 14, wherein the initialization is triggered by an acceleration impulse corresponding to when the swimmer pushes of a wall of the swimming pool structure to start each new lap.

18. The method defined in claim 14, further comprising determining in real-time the swimmer's mode of activity from at least one of the swimmer's body orientation and the three-dimensional acceleration measurements, wherein the mode of activity is selected from a group comprising:

diving;
gliding;
stroking;
standing;
turning;
pushing off a wall; and
stopping.

19. The method defined in claim 15, wherein incrementing the timer comprises incrementing a split timer that resets when the swimmer's mode of activity is pushing off the wall of the swimming pool structure or diving; and periodically storing the split timer values.

20. The method defined in claim 16, further comprising counting the number of times the swimmer's mode of activity is stroking between a consecutive pair of split timer resets.

21. The method defined in claim 14, further comprising calibrating the swimmer's speed in the forward direction based on location measurements of the swimmer made by a GPS receiver.

* * * * *